March 17, 1964 F. W. ANDERSON Plant Pat. 2,379
ALMOND TREE
Filed March 29, 1963
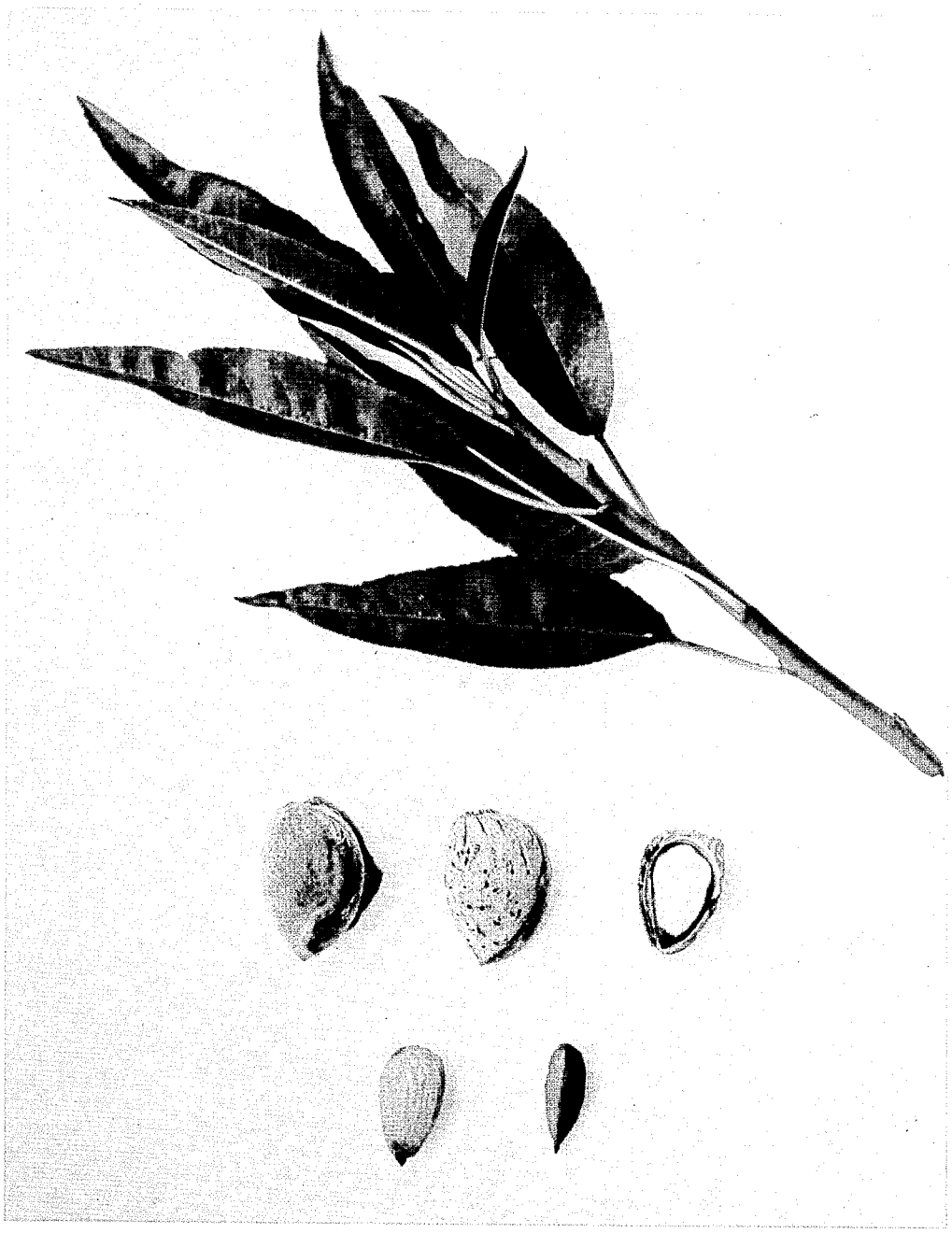
INVENTOR
*Frederic W. Anderson*
BY *Webster & Webster*
ATTYS.

United States Patent Office

Plant Pat. 2,379
Patented Mar. 17, 1964

2,379
ALMOND TREE

Frederic W. Anderson, Merced, Calif., assignor to Irvin M. Burchell, doing business as The Burchell Nursery, Modesto, Calif.

Filed Mar. 29, 1963, Ser. No. 269,223
1 Claim. (Cl. Plt.—30)

This invention relates to a new and distinct variety of almond tree characterized, as to novelty, by a tree having great vigor; by a relatively late blooming period; by an excellent spur system; and by high production of commercially acceptable nuts.

The variety is further characterized, in comparison with the IXL variety, by a blooming period approximately two weeks later; by general resemblance of the nuts in shape and color, but usually of a smaller size; and by substantially heavier production which seems to be correlated to the vigor of the tree, its relatively late blooming period, and its superior spur system, all as aforesaid.

The variety is additionally characterized by interfertility—as is desirable—with numerous commercial varieties including the Nonpareil, Mission, Drake, Ruby (United States Plant Patent No. 1,698), and Emerald (United States Plant Patent No. 2,208).

I originated the herein claimed variety of almond tree, as an open pollinated seedling, and under careful and continuing observation, in my experimental nursery and orchard located near Le Grand, in the county of Merced, California, in the following manner:

Several thousand nuts of an unnamed almond variety, which seemed identical to the Nonpareil except for a blooming period about two weeks later, were planted. Those that germinated earliest (about one-half the total) were removed and destroyed on the possibility that early germination is correlated with early leafing and early blooming.

At the start of the second growing season, about three-fourths of those of the remaining seedlings which leafed out earliest were also removed and destroyed. Those that then remained were permitted to continue growing and most of them produced blossoms during the third season; those that appeared to blossom earlier than the Mission, having been removed and destroyed.

At this point, several hundred trees remained and they were allowed to mature and produce nuts; the majority of this group also having been removed and destroyed because of various shortcomings such as lack of vigor or productiveness of the trees, bitterness of the kernels, double or defective kernels, and open or very soft shells which permitted access to the kernel by moisture, fungi, dust, insects, and birds.

Of the trees retained from such group, the present variety was selected as having substantial commercial potential; the variety having been found to be substantially free from the above described shortcomings, and to evidence the novel and desirable characteristics hereinbefore described.

Subsequent to origination and selection of the variety, I asexually reproduced it in my experimental orchard, located as aforesaid, by top-working on mature trees; such reproductions having run true to the parent in all respects.

The drawing comprises an illustration, by photographic reproduction in color, of a first year shoot with leaves; a nut with the hull thereon; a nut with the hull removed; a nut with half the shell removed and the kernel cut to expose the meat; a kernel from one side; and another kernel from one edge.

Referring now more specifically to the botanical details of this new and distinct variety of almond tree, the following is an outline description thereof; all major color plate identifications, by comparison with fresh specimens, being by reference to Maerz and Paul Dictionary of Color, except where common terms of color definition are employed:

Tree:
- *Density.*—Open.
- *Size.*—Large.
- *Vigor.*—Vigorous.

Trunk:
- *Form.*—Medium.
- *Texture.*—Medium.

Branches:
- *Form.*—Medium.
- *Texture.*—Medium.
- *Branching habit.*—Medium.

Foliage: Quantity—abundant.

Leaves:
- *Size.*—Medium to large. Average length—3″. Average width—1″.
- *Shape.*—Ovate.
- *Thickness.*—Medium.
- *Texture.*—Smooth.
- *Margin.*—Crenate.
- *Petiole.*—Medium length.
- *Glands.*—Average number—two, varying from one to four. Position—alternate; usually on petiole but sometimes one or two at base of blade. Size—medium.
- *Color.*—Medium green (23–H–5).

Bloom:
- *Amount of bloom.*—Very heavy.
- *Color.*—White.
- *Blooming period.*—About with Mission, and approximately two weeks later than IXL.

Crop:
- *Bearing.*—Regular bearer.
- *Productivity.*—Very heavy.
- *Distribution of nuts on tree.*—Well distributed.
- *Harvest period.*—About with Ne Plus Ultra but somewhat later than Nonpareil.
- *Tenacity.*—Hangs well on tree; easy to harvest; easy to hull.

Hull:
- *Outer surface.*—Smooth.
- *Form.*—Regular.
- *Thickness.*—Thin.
- *Color.*—At harvest—gray green (15–H–4).
- *Dehiscense.*—Opens freely.
- *Splitting.*—Along suture.

Nut:
- *Size.*—Medium to small. Average length—1¼″. Average width—⅞″. Average thickness—⅝″.
- *Nuts per pound on average sample.*—240.
- *Form.*—Length/width—ovate. Width/thickness—medium.
- *Shell.*—Hard. Outer shell—hard. Inner shell—hard; well sealed.
- *Color.*—Light beige (11–D–4).
- *Pits.*—Small; numerous; shallow; round.
- *Base.*—Square.
- *Stem scar.*—Large.
- *Apex.*—Obtuse; blunt; tip recurved.
- *Wing.*—Narrow.
- *Inner surface.*—Light.
- *Ventral streak.*—Dark; broad; long; point acute.

Kernel:
- *Size.*—Medium to small. Average length—⅞″. Average width—9/16″. Average thickness—5/16″.
- *Kernels per ounce on average sample.*—30.

*Form.*—Length/width—wedge. Width/thickness—medium to flat.
*Base.*—Square.
*Stem scar.*—Small.
*Apex.*—Obtuse; blunt.
*Surface.*—Furrowed.
*Pellicle.*—Thin.
*Pubescence.*—Medium.
*Color.*—Light tan (13–L–10).
*Number of doubles.*—None to few.
*Defective kernels.*—Very few of any kind, but occasional creases in kernels.
*Flavor.*—Normal.
*Quality.*—Good.

Except where otherwise indicated, all of the herein identified existing varieties of almond trees are unpatented.

The tree and its nuts herein described may vary slight detail due to climatic and soil conditions under which this variety may be grown; the present description being of the variety as grown in the Central Valley of California.

The following is claimed:

A new and distinct variety of almond tree, substantially as illustrated and described, characterized by vigor of growth, by a relatively late blooming period, by an excellent spur system, and by high production; and further characterized in comparison with the IXL by a blooming period approximately two weeks later, by general resemblance of the nuts in shape and color but usually of smaller size, and by substantially heavier production.

No references cited.